United States Patent [19]

Muller et al.

[11] Patent Number: 5,509,421
[45] Date of Patent: Apr. 23, 1996

[54] SYSTEM, WITH SENSOR POSITIONING INDICATOR, FOR MONITORING A BIOLOGICAL SIGNAL

[75] Inventors: Jeremy L. Muller, Pelham, N.H.; Gordon W. Neff, Lexington, Mass.; Joseph T. Pappalardo, Magnolia, Mass.; G. Peter Pulsifer, Dracut, Mass.

[73] Assignee: Analogic Corporation, Peabody, Mass.

[21] Appl. No.: 428,719

[22] Filed: Apr. 25, 1995

[51] Int. Cl.⁶ ................................................ A61B 8/00
[52] U.S. Cl. .................................... 128/662.04; 128/698
[58] Field of Search ........................ 128/661.07, 661.08, 128/661.09, 698, 662.04

[56] References Cited

U.S. PATENT DOCUMENTS

| | | | |
|---|---|---|---|
| 3,991,365 | 11/1976 | Takeuchi | 128/661.07 |
| 4,086,916 | 5/1978 | Freeman et al. | |
| 4,367,752 | 1/1993 | Jimenez et al. | |
| 4,459,992 | 7/1984 | Gwyn | |
| 4,781,200 | 11/1988 | Baker | |
| 5,103,825 | 4/1992 | Hokanson et al. | |
| 5,257,627 | 11/1993 | Rapoport | 128/661.07 |

Primary Examiner—George Manuel
Attorney, Agent, or Firm—Lappin & Kusmer

[57] ABSTRACT

The invention is a physiological monitor for determining a physiological characteristic of a patient. The monitor is particularly adapted to monitor fetal heart rate, and includes a transducer for receiving a signal from the patient that is indicative of the physiological characteristic and for generating an output signal that is representative of the received signal. The monitor further includes a processor coupled to the transducer for receiving the output signal and generating therefrom a physiological signal that is representative of the physiological characteristic. The physiological signal may further be representative of the signal strength of a signal used to calculate the physiological characteristic. The monitor further includes a display unit fixed to the transducer and coupled to the processor for generating a display representative of the physiological signal.

17 Claims, 4 Drawing Sheets

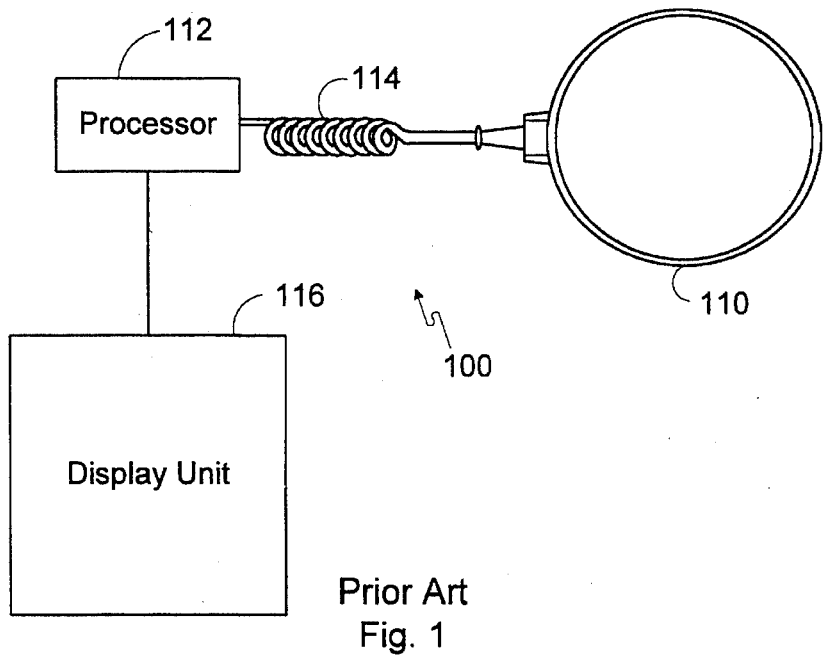
Prior Art
Fig. 1
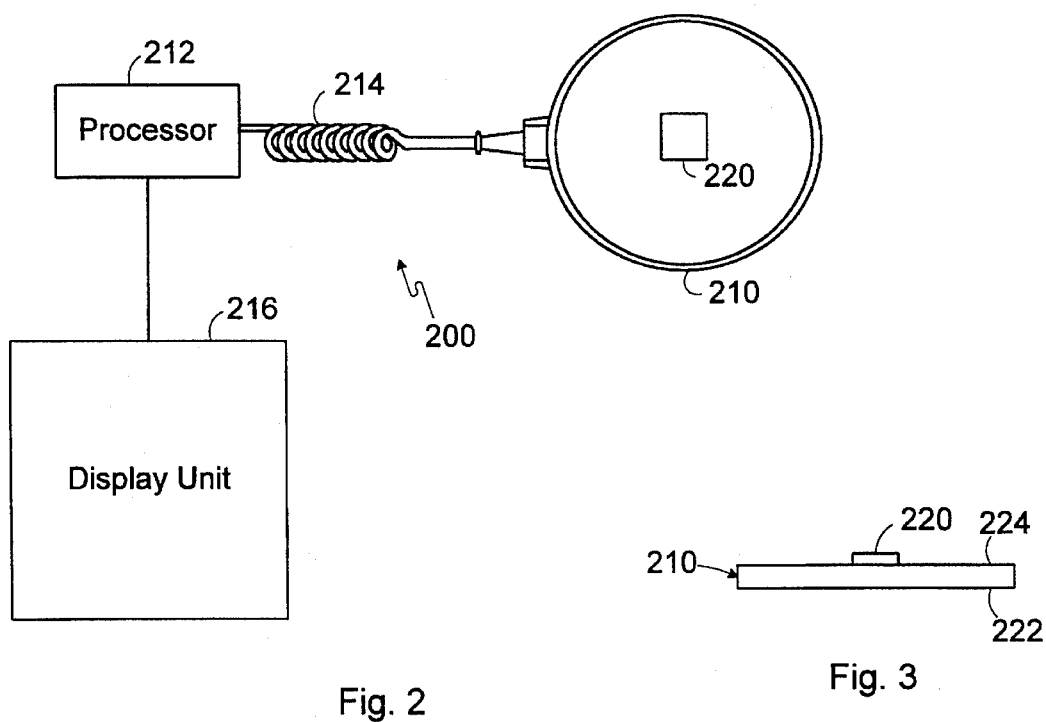
Fig. 2
Fig. 3

SYSTEM, WITH SENSOR POSITIONING INDICATOR, FOR MONITORING A BIOLOGICAL SIGNAL

FIELD OF THE INVENTION

The present invention relates generally to a system for monitoring a biological characteristic of a patient, and more particularly to such a system including a sensor positioning indicator for facilitating the optimum placement of the sensor in order to reliably sense a signal representative of that characteristic.

BACKGROUND OF THE INVENTION

Various monitors are known for measuring biological or physiological characteristics of a patient. Most of these monitors include some type of sensor for sensing a biological signal representative of the characteristic. The sensor usually includes a transducer and often is coupled by a flexible cable to a processor and a display unit for displaying information about the monitored biological signal. One important class of such monitors is ultrasound fetal monitors commonly used for detecting and displaying the heart rate and other physiological characteristics of a fetus in vivo. In operation, the hand held sensor containing the transducer of such a monitor is typically positioned on the abdomen of the mother by a skilled operator, such as a physician or attending nurse. The accuracy of such monitors degrades quickly as the transducer is moved away from an optimal location on the abdomen, so it is important that the transducer be positioned accurately. The fetus is often active and frequently moves within the womb making optimum placement of the transducer sometimes difficult and time consuming, when the exact position of the fetus is unknown. When activated, the transducer generates ultrasound signals that penetrate the body of the mother. The transducer also receives ultrasound echoes that are reflected by the fetus, as well as by internal structures of the mother's body, and generates electrical signals representative of the received ultrasound signals. While the range and direction of the transmitted ultrasound can be controlled between certain limits, they are usually quite limited so that if the sensor is incorrectly positioned relative to the fetus, no echoes from the fetus will be sensed. If correctly positioned, the transducer will convert the ultrasound echo signals representative of the heart beat of the fetus into an electrical signal which is transmitted over the flexible cable to the processor. The processor analyzes these electrical signals to determine the heart rate and other physiological characteristics of the fetus. The output of the monitor, including an indication of the fetal heart rate, is visually displayed by the display unit which may be implemented as a cathode ray tube type display or a light emitting diode (LED) type display, or the like. The display unit is typically positioned remotely from the transducer on a shelf or a cart.

Prior art fetal monitors suffer from the disadvantage that the operator can not conveniently view the output of the display unit while positioning the transducer. Since the accuracy of such monitors degrades rapidly as the transducer is moved away from an optimum position, it is important that the operator watch the display unit to evaluate whether the heart beat is being sensed and whether the strength of the sensed signal is adequate. Typically, the operator places the transducer on the patient and then, while holding the transducer in place, turns to view the display unit. By viewing the output of the display unit, the operator can determine whether the transducer is positioned optimally. If the transducer is not optimally positioned, the operator then either continually moves the transducer while watching the display, or looks at the display between successive movements of the transducer, trying to find the optimal position of the transducer, where the signal strength of the echoes is at a maximum or near maximum, or at least sufficiently strong so that the processor can accurately process the signal information sensed by the transducer. In any case the operator takes his or her eyes off the patient, which can make the patient uncomfortable. The process of adjusting the position of the transducer is repeated until the operator determines that the transducer is positioned sufficiently well for the monitor to function accurately. Once the transducer is so positioned, the transducer is usually fixed to the mother by a strap, or tape, or the like. While being monitored, should the fetus move sufficiently away from the sensor, the process must be repeated. Such monitors are therefore awkward and inconvenient to operate, because the operator must, either take his or her eyes off the patient, or continually turn back and forth between the transducer and the display unit when positioning the transducer.

OBJECTS OF THE INVENTION

Accordingly it is a primary object of the present invention to provide a physiological monitor that is convenient to operate.

Another object of the present invention is to provide a physiological monitor having a sensed signal indicator mounted on or within the view of the hand held sensor.

Yet another object of the present invention is to provide an ultrasound fetal heart monitor having sensed signal indicator mounted on or within the view of the sensor so that both the sensor and indicator are within the view of the operator when the sensor is being moved.

Still another object of the present invention to provide an ultrasound fetal heart monitor having a display mounted on the sensor that is indicative of the fetal heart rate.

Another object of the present invention is to provide an ultrasound fetal heart monitor having a display mounted on the sensor that is indicative of the signal quality of the measured heart rate signal.

Other objects and advantages of the present invention will become apparent upon consideration of the appended drawings and description thereof.

SUMMARY OF THE INVENTION

These and other objects are achieved by a physiological monitor having an indicator fixed within the view of, and preferably fixed to the sensor for indicating whether the transducer is sufficiently well placed for receiving signals from the patient that are representative of physiological characteristics of the patient. Preferably, the indicator indicates the degree of signal strength, e.g., strong, weak or undetected, and preferably includes the means for visually displaying the signal information detected, e.g., fetal heart rate. The need to view a display unit that is remote from the transducer while positioning the transducer is thereby eliminated.

BRIEF DESCRIPTION OF THE DRAWINGS

For a fuller understanding of the nature and objects of the present invention, reference should be had to the following detailed description taken in connection with the accompanying drawings wherein:

FIG. 1 is a block diagram of a prior art physiological monitor;

FIG. 2 is a block diagram of a physiological monitor constructed according to the principles of the present invention;

FIG. 3 is a side view of a sensor and sensor positioning indicator constructed according to the principles of the present invention;

DETAILED DESCRIPTION OF THE DRAWINGS

Figure 4:
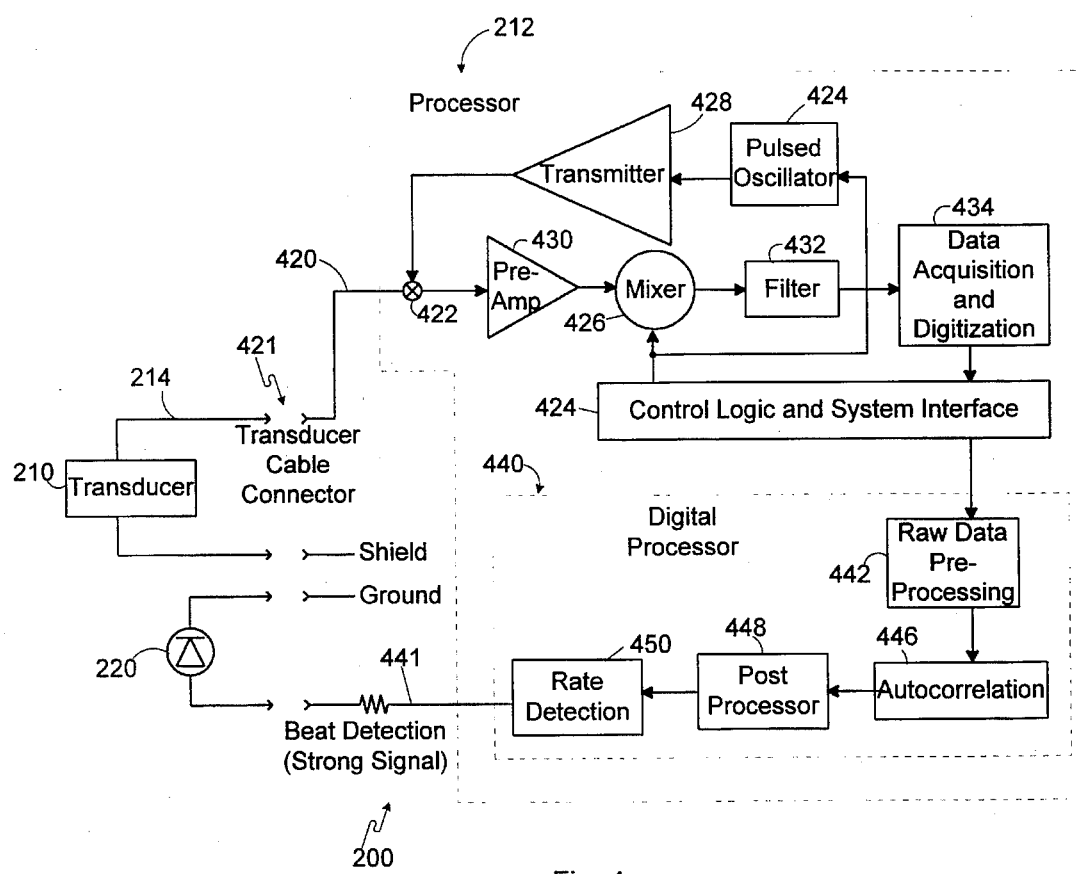
FIG. 4 is a block diagram of a fetal heart rate monitor constructed according to the invention illustrating the internal structure of the processor which is used for calculating fetal heart rate.

FIG. 1 illustrates a prior art physiological monitor 100. Monitor 100 has a sensor including a transducer, generally represented at 110, that is coupled to a processor 112 via a flexible cable 114. Processor 112 is further coupled to a display unit 116. The display unit displays the output generated by the processor and may also display unprocessed signals received directly from the transducer of the sensor 110. Typically, the display unit displays information relating to one or more physiological characteristics with respect to a patient, e.g., biological rhythmic signals, such as the heart rate of a fetus. In general, the operator of the monitor must look at the display unit 116, while moving the transducer over the patient, or between movements, to find the optimal position of the transducer where the maximum strength of the echoes is received. Such a procedure can make the patient feel uncomfortable, and in some cases make it difficult to locate the optimal position.

FIG. 2 illustrates a physiological monitor 200 constructed according to the invention, and, especially adapted for fetal monitoring. Monitor 200 has a sensor 210, that is coupled to a processor 212 via a flexible cable 214. In accordance with the present invention, monitor 200 also has an indicator unit 220 that is fixed to one side of sensor 210. Sensor 210 may also have an additional indicator unit 216.

FIG. 3 is a side view of sensor 210. In operation, one side 222 of sensor 210 is placed in contact with the patient's body so as to receive signals from the patient. Indicator unit 220 is mounted on the other side 224 of sensor 210.

In one preferred embodiment, monitor 200 is an ultrasound fetal monitor used for monitoring physiological characteristics in the form of biological rhythmic signals such as the heart beat of a fetus in vivo. In this embodiment, sensor 210 includes an ultrasound transducer that emits and receives ultrasound signals from side 222. In operation, an operator places side 222 adjacent the mother's abdomen. The transducer of sensor 210 emits ultrasound signals that penetrate the mother's body and also receives ultrasound echo signals that are reflected by the fetus and other structures of the mother's body in a manner well known in the art. The transducer of sensor 210 generates output information signals representative of the received ultrasound signals. Cable 214 transmits these output information signals to processor 212 which processes them to determine the heart rate of the fetus, and may further determine other physiological characteristics of the fetus and the mother, such as the mother's heart rate. Processor 212 then transmits a signal via cable 214 to indicator unit 220 indicative of either the fetal heart rate or the signal strength of the measured heart rate signal, or both. By viewing the output of indicator unit 220, the operator can determine whether the transducer of sensor 210 should be repositioned to a more optimal location on the mother's abdomen. Indicator unit 220 thus eliminates the need for the operator to turn and view a remote display (such as display unit 116 shown in FIG. 1) when positioning the transducer.

FIG. 4 is a block diagram of one preferred embodiment of ultrasound fetal monitor 200 showing the sensor 210 and the internal structure of processor 212 which is used for calculating the fetal heart rate detected by the transducer of sensor 210. The transducer is properly shielded and connected through flexible cable 214 (shown in FIG. 2) to connector 421, which in turn is connected through line 420 to the input/output of the processor 212. The input/output of the processor 212 includes a bistable T/R switch 422, which when set in a transmit mode transmits signals over line 420 and flexible cable 214 to the transducer of sensor 210 for generating the ultrasound signals into a patient's body, and when set in a receive mode receives signals from the transducer of sensor 210 over cable 214 and line 420 and representative of the echoes received by the transducer from the patient's body.

Processor 212 comprises a control logic and system interface 424 for applying a carrier signal to a pulsed oscillator 424 and to a signal mixer 426. Pulsed oscillator 424 applies pulsed oscillating signals to the input of a transmitter 428, the output of which is coupled to one terminal (the transmit side) of switch 422 so that when switch 422 is switched to its transmit mode, transmits signals at the output of transmitter 428 appear the output of the processor 212. Another terminal (the receive side) of switch 422 is coupled to an input of a pre-amplifier 430 for amplifying signals received from the transducer of sensor 210. The output of the pre-amplifier 430 is coupled to an input of signal mixer 426. The output of mixer 426 is applied to an input of a filter 432, the output of the latter being applied to a data acquisition and digitization section 434 for further processing of the received signal. The digital output of data acquisition section 434 is applied to the control logic and system interface 424. Control logic and system interface 424 applies a signal to an input of a digital processor 440 for generating a beat detection signal over line 441 to indicator unit 220, indicative of signal strength. The input signals from section 434 to digital processor 440 are processed by a pre-processor 442. The output of pre-processor 442 is applied to an autocorrelation processor 446, the output of the latter being applied to a post processor 448. A rate detection processor 450 evaluates the output of post processor 448 and generates beat detection signal on line 441 to indicator unit 220.

In operation, processor 212 transmits signals to and receives signals from transducer of sensor 210. During the transmit mode of operation, system interface 424 controls the T/R switch 422 so that it is set in the transmit mode so as to couple the output of transmitter 428 to line 420. Processor 212 transmits signals to the transducer of sensor 210 by using the control logic and system interface 424 to generate and apply a carrier signal to pulsed oscillator 424 which in turn applies a signal to transmitter 428. Transmitter 428 generates an analog signal which is applied to the transducer of sensor 210 via switch 422 and which causes the transducer of sensor 210 to emit ultrasound signals.

During the receive mode of operation, system interface 424 controls T/R switch 422 so that it is set in the receive mode so as to couple line 420 to the input of pre-amplifier 430. Transducer 210 receives reflected ultrasound echo signals and converts them to electrical signals that are transmitted to processor 212. Processor 212 receives signals from transducer 210 via switch 422 with pre-amplifier 430. Mixer 426 uses a carrier signal applied by system interface 424 to demodulate the output of pre-amplifier 430. The demodulated output of mixer 426 is then applied to an analog filter 432, the output of which is converted to a digital signal and then sampled by data acquisition and digitization stage 434. This digital output is then applied to digital processor 440 via system interface 424.

Digital processor 440 uses pre-processor 442 to suppress signals having frequencies outside the frequency range of a fetal heart rate (e.g., a range from approximately 50 beats per minute to approximately 200 beats per minute). Autocorrelation processor 446 uses autocorrelation processing to filter noise from the output of pre-processor 442, and then post processor 448 is used to evaluate the autocorrelation function to determine signal strength and to generate a list of likely heart rates. The output of autocorrelation processor 446 is indicative of the fetal heart rate and may be thought of as a measured heart rate signal. The signal strength of the output of autocorrelation processor 446 is indicative of the strength of the measured heart rate signal. Rate detection processor 450 processes the output of post processor 448 to determine the fetal heart rate and generates on line 441 a beat detection signal which in turn is applied to indicator unit 220.

In one preferred embodiment, post processor 448 generates a signal indicative of the signal to noise ratio of the output of the autocorrelation processor 446. In another preferred embodiment, post processor 448 generates a signal indicative of whether the signal strength of the output of the autocorrelation processor 446 is above a predetermined threshold. In the latter embodiment, signals above the threshold indicate that the processor 212 has determined the fetal heart rate, and signals below the threshold indicate that the processor 212 has not determined the fetal heart rate. In yet another embodiment, post processor 448 compares the signal strength of the output of the autocorrelation processor 446 to two thresholds. If the signal strength is below the lower threshold, then the post processor 448 generates a signal that indicates that processor 212 has not determined the heart rate. If the signal strength is greater than the lower threshold and lower than the upper threshold, then post processor 448 generates a signal that indicates that processor 212 has determined the heart rate but that the measured heart beat is a weak signal. If the signal strength is greater than the upper threshold, then post processor 448 generates a signal that indicates that processor 212 has determined the heart rate and that the measured heart beat is a strong signal. In this embodiment, a strong signal indicates that the transducer is well placed and that the operator can have a high degree of confidence that monitor 200 is accurately measuring the fetal heart rate. A weak signal, and a signal indicating that the processor has not determined the heart rate, indicate that the transducer is not in an optimal location and the operator should consider repositioning the transducer.

As those skilled in the art will appreciate, FIG. 4 illustrates one embodiment of a processor for determining the fetal heart rate and for determining the signal strength of a signal that is used for determining the fetal heart rate. These signals may alternatively be generated by a variety of other processors and techniques that are known in the art.

Figure 5A:
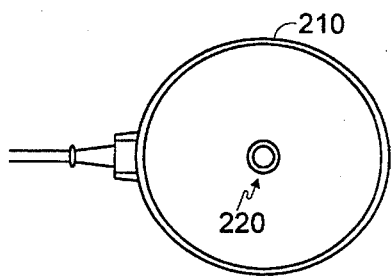
FIGS. 5A–C are illustrations of various embodiments of sensor positioning indicators in the form of various displays for use in connection with physiological monitors constructed according to the principles of the present invention.
Figure 5B:
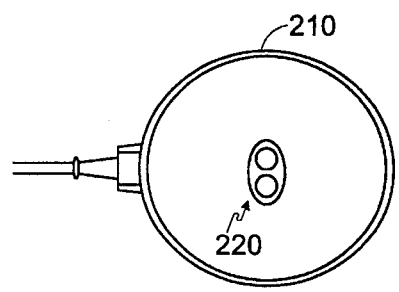
Figure 5C:
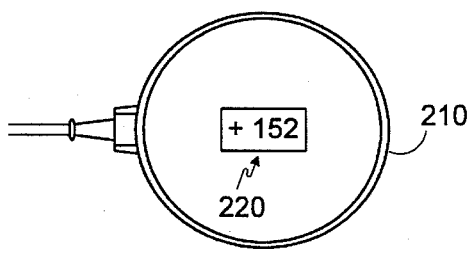

FIGS. 5A–C illustrate different embodiments of the preferred indicator unit 220, all shown and described as visual displays. In FIG. 5A, indicator unit 220 may be implemented as a single Light Emitting Diode (LED) or as a dual colored (back to back) LED. In the single LED embodiment, the processor may cause the LED to flash at the frequency of the fetal heart rate when the processor has determined the heart rate, and may cause the LED to remain unlit when the processor has not determined the heart rate. In the dual colored LED embodiment, the processor may cause the LED to flash in one color when the measured fetal heart rate signal is a strong signal, and to flash in the other color when the measured fetal heart rate signal is a weak signal, and to remain unlit when the processor has not determined the heart rate.

FIG. 5B illustrates a preferred embodiment in which indicator unit 220 is implemented as two LEDs. In one embodiment, the processor causes one of the LEDs to flash at the frequency of the detected fetal heart rate to indicate that the measured heart rate signal is a strong signal, and causes the other LED to flash to indicate that the measured heart rate signal is a weak signal, and causes both LEDs to remain unlit to indicate that the processor has not determined the heart rate.

In alternative embodiments in which indicator unit 220 is implemented using one or more LEDs, the processor may cause the LED to flash at a frequency other than the heart rate, or may simply light the LED with a steady signal, to indicate that the heart rate has been detected.

FIG. 5C illustrates an embodiment in which indicator unit 220 is implemented as an alpha-numeric display, such as a liquid crystal display (LCD). In one embodiment, the processor displays the detected heart rate numerically on such a display. The processor may also provide an indication of the signal strength of the detected heart rate signal. For example, the processor may display a "+" (plus) sign on indicator unit 220 to indicate a strong signal and may display a "–" (minus) sign to indicate a weak signal. Further, the processor may provide another indication when the measured heart rate signal is too weak to detect the heart beat. For example, the processor may display three dashes "- - -" to indicate that the processor has not determined the heart rate. Alternatively, the processor may display the signal to noise ratio of the measured heart rate signal on the LCD display. As those skilled in the art will appreciate, many other displays indicative of the heart rate and/or the signal strength of the measured heart rate signal are possible and are within the scope of the invention, including combinations of the above-described displays.

Figure 6A:
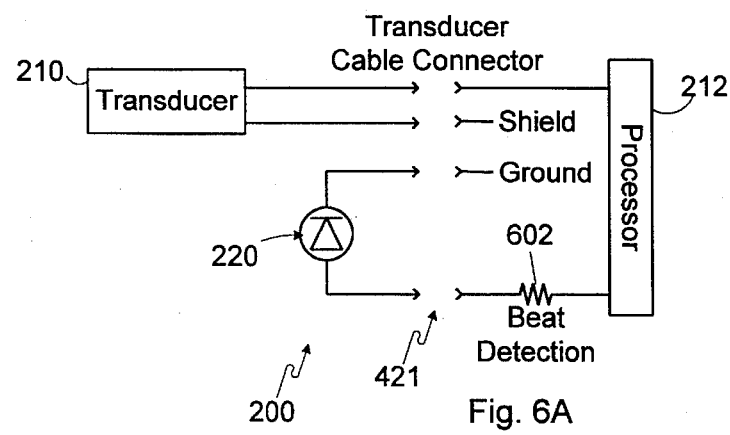
FIGS. 6A–D are partial block and partial schematic diagrams illustrating circuitry for controlling various display units for use with physiological monitors constructed according to the principles of the present invention.

FIGS. 6A–D illustrate various embodiments of fetal heart monitor 200 showing different structures for controlling indicator unit 220. FIG. 6A shows an embodiment in which indicator unit 220 is implemented as a single LED. Processor 212 generates a beat detection signal that is coupled through a resistor 602 to one terminal of the LED via connector 421, and the other terminal of the LED is coupled to ground. Processor 212 controls the LED simply by driving the beat detection signal to ground level to make the LED unlit, and by driving the beat detection signal to a high voltage (e.g., five volts) to light the LED.

Figure 6B:
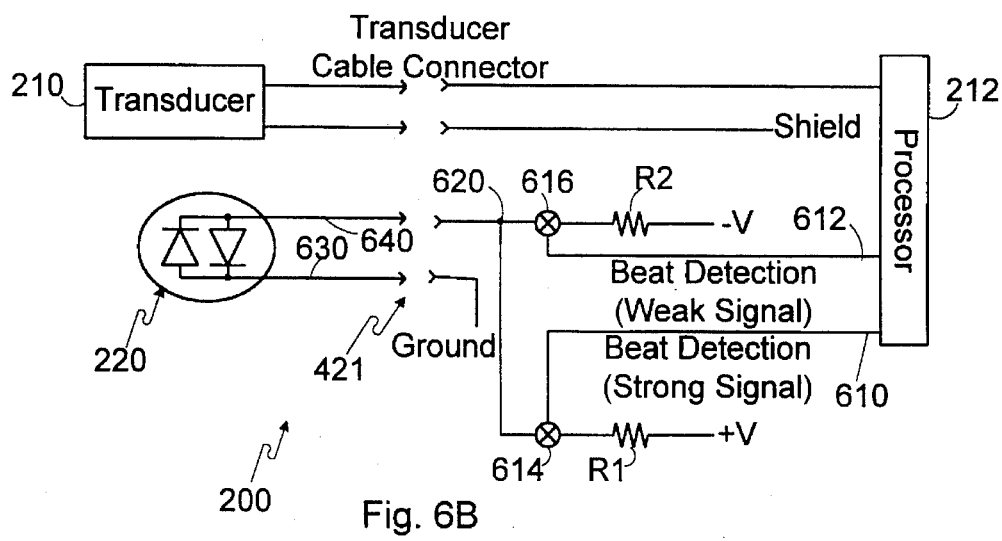

FIG. 6B illustrates an embodiment in which indicator unit 220 is implemented as a dual color LED. Processor 212 generates two beat detection signals, a beat detection signal on line 610, the signal being indicative of a strong detected heart rate signal, and a beat detection signal on line 612, the latter signal being indicative of a weak detected heart rate signal. The signal on line 610 is applied to the control terminal of a switch 614, and the signal on line 612 is applied to the control terminal of a switch 616. The output terminals of switches 614 and 616 are tied together to form a node 620. A positive voltage supply +V is coupled through a resistor R1 to the input terminal of switch 614, and a negative voltage supply −V is coupled through a resistor R2 to the input terminal of switch 616. One terminal line 630 of indicator unit 220 is coupled to ground level via connector 421 and the other terminal line 640 of indicator unit 220 is coupled to node 620 via cable connector 421. When processor 212 drives the signal on line 610 to a high level (e.g., five volts) converting switch 614 to a closed condition, switch 614 couples the positive supply +V to node 620. When processor 212 drives the signal on line 610 to a low level (e.g., ground) switch 614 remains open so as to maintain an open circuit between node 620 and the positive supply +V. When processor 212 drives the signal on line 612 to a high level converting switch 616 to a closed condition, switch 616 couples negative supply −V to node 620. When processor 212 drives the signal on line 612 to a low level, switch 616 maintains an open circuit between node 620 and the negative supply −V. So, by driving signal 610 to a high level, processor 212 couples the positive supply +V to terminal 640 and lights one of the two LEDs, and by driving signal 612 to a high level, processor 212 couples the negative supply −V to terminal 640 and lights the other of the two LEDs of indicator unit 220. This implementation allows processor 212 to control a two color display using only one wire of connector 421 (and therefore of flexible cable 214, which is shown in FIG. 2). This wire couples node 620 to the terminal line 640. An additional wire to couple terminal 630 to ground level is not required since a wire at ground level is typically already required in cable 214 for use with the transducer of sensor 210.

Figure 6C:
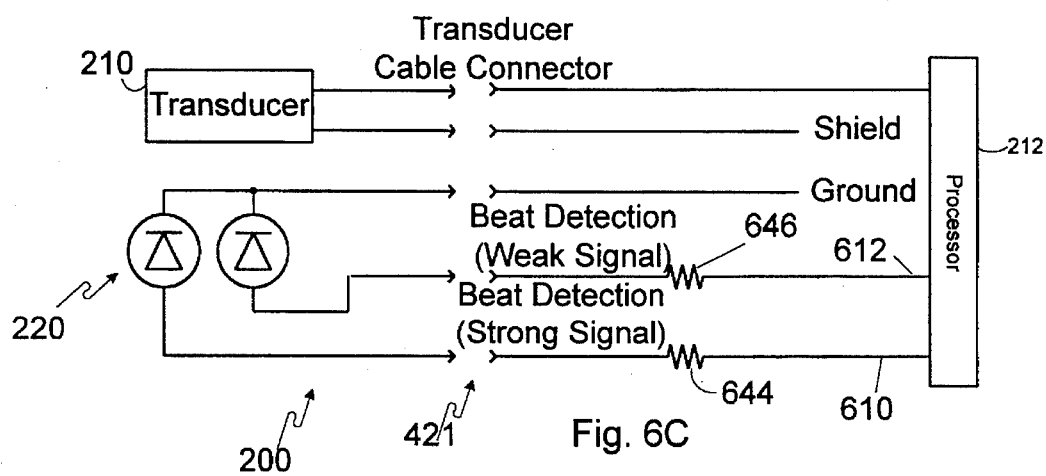

FIG. 6C illustrates an embodiment in which indicator unit 220 is implemented as two LEDs. One terminal of each of the LEDs is coupled to ground level via connector 421. Processor 212 generates two beat detection signals; a beat detection signal on line 610 indicative of a strong measured heart beat, and a beat detection signal on line 612 indicative of a weak measured heart beat. The beat detection signal on line 610 is applied through a resistor 644 to one terminal of one of the LEDs and the beat detection signal on line 612 is applied through a resistor 646 to one terminal of the other LED via connector 421.

Figure 6D:
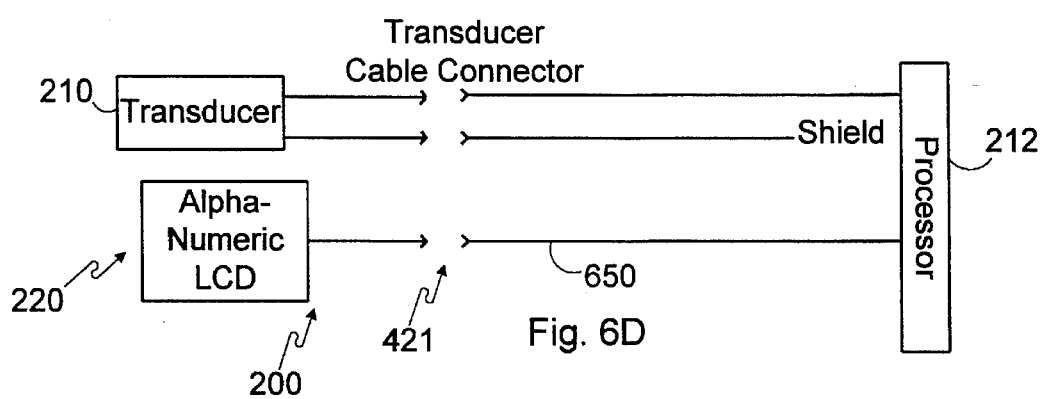

FIG. 6D illustrates an embodiment in which indicator unit 220 is implemented as an alpha-numeric LCD display. Processor 212 generates an interface signal on line 650, which may be a parallel or serial interface signal. The line 650 is coupled to the input of the LCD display via connector 421.

The invention has been discussed in terms of an ultrasound fetal heart monitor. As those skilled in the art will appreciate, the invention also encompasses other forms of physiological monitors for detecting and/or monitoring physiological signals which are difficult to detect and/or require optimal positioning of a sensor which can vary from patient to patient or from time to time. For example, in some embodiments the transducer may be a passive transducer, such as an EKG electrode that collects information from the patient and does not transmit signals that penetrate the body of the patient. In still other embodiments, monitors according to the invention may be used to measure other physiological characteristics, such as respiration rate.

In addition, the preferred indicator unit has been described as a visual display, but the indicator unit could provide signals from the sensor, such as aural signals, which the operator detects by other senses.

The ultrasound fetal monitor comprising the sensor positioning indicator mounted on or within the view of the hand held sensor in accordance with the present invention is convenient to operate. Both the sensor and indicator can be simultaneously viewed by the operator facilitating placement of the sensor in an optimal position. The sensor indicator can provide information relating to signal strength as well as data relating to the physiological characteristic being monitored, such as fetal heart rate.

Since certain changes may be made in the above apparatus without departing from the scope of the invention herein involved, it is intended that all matter contained in the above description or shown in the accompanying drawing shall be interpreted in an illustrative and not a limiting sense.

What is claimed is:

1. A system for monitoring a biological signal, representative of a physiological characteristic, from a living body, the system being of the type including sensing means, positionable on the living body, for sensing the biological signal and for generating an electrical signal representative of the biological signal; and processing means, coupled to said sensing means, for processing said electrical signal; said system further comprising:
   indicator means, spatially fixed relative to and within the view of said sensing means, for indicating whether said sensing means is sensing the biological signal as the sensing means is moved relative to and positioned on the living body.

2. A system according to claim 1, wherein said system is for monitoring a biological rhythmic signal, and said processing means includes means for determining whether said biological rhythmic signal as sensed by said sensing means exceeds a predetermined level.

3. A system according to claim 1, wherein said system is for monitoring the total heart beat of a fetus within its mother's body, said sensing means is positionable on the mother's body so as to be optimally positioned for sensing the fetal heart beat, and said indicator means includes means for indicating whether said sensing means is sensing the fetal heart beat as the sensing means is moved and positioned on the mother's body.

4. A system according to claim 3, wherein said indicator means includes display means for displaying a visual indication within the visual field of said sensing means of whether said sensing means is sensing the fetal heart beat.

5. A system according to claim 4, wherein said sensing means includes transducer means for sensing the fetal heart beat.

6. A system according to claim 5, wherein said transducer means includes a passive device for sensing the fetal heart beat.

7. A system according to claim 5, wherein said transducer means includes an active acoustic device for generating a transmitted acoustic signal into the mother's body and for receiving acoustic signals from the mother's body in response to the transmitted acoustic signal.

8. A system according to claim 7, wherein said acoustic device is an ultrasound transducer.

9. A system according to claim 7, wherein said processing means includes means for generating a drive signal to said active acoustic device, so that said acoustic device generates said transmitted acoustic signal in response to said drive signal.

10. A system according to claim 4, wherein said display means includes means for providing a visual indication whether the strength of the fetal heart beat as sensed by said sensing means is above a predetermined threshold.

11. A system according to claim 4, wherein said display means includes means for providing a visual indication whether the strength of the fetal heart beat as sensed by said sensing means is between a first and second predetermined threshold, and whether the strength of the fetal heart beat as sensed by said sensing means is above said second predetermined threshold.

12. A system according to claim 4, wherein said indicator means includes display means for displaying the fetal heart rate of the fetus as sensed by said sensing means and processed by said processing means when the fetal heart beat as sensed by said sensing means is above a predetermined threshold.

13. A system according to claim 12, wherein said display means further includes means for providing a visual indication whether the strength of the fetal heart beat as sensed by said sensing means is between a first and second predetermined threshold, and whether the strength of the fetal heart beat as sensed by said sensing means is above said second predetermined threshold.

14. A system according to claim 4, wherein said indicator means includes means for pulsing said display means when said sensing means is sensing the fetal heart beat.

15. A system according to claim 14, wherein said means for pulsing said display means pulses said display means at the sensed fetal heart rate.

16. An ultrasound fetal monitor for determining the heart rate of a fetus within the mother's body, said monitor comprising:

a transducer unit, positionable on the mother's body, for generating an ultrasound signal into the mother's body and for generating an output signal representative of an ultrasound signal reflected by the fetus and received by the transducer unit in response thereto;

a processor coupled to the transducer unit for receiving the output signal and generating therefrom a processed signal representative of the heart rate of the fetus; and display means, fixed to the transducer unit, coupled to the processor and responsive to said processed signal, for generating a display representative of the processed signal.

17. An ultrasound fetal monitor for determining the heart rate of a fetus that is within a mother's body, said monitor comprising:

a transducer unit, positioned on the mother's body, for generating an ultrasound signal into the mother's body and for generating an output signal representative of an ultrasound signal reflected by the fetus and received by the transducer unit in response thereto, the received ultrasound signal being representative of the heart beat of the fetus;

a processor, coupled to the transducer unit for receiving the output signal and for processing the output signal so as to generate a indicator signal indicative of whether the heart rate of the fetus has been measured; and display means fixed to the transducer unit and coupled to the processor for generating a display on said transducer unit representative of the indicator signal.

* * * * *

UNITED STATES PATENT AND TRADEMARK OFFICE
CERTIFICATE OF CORRECTION

PATENT NO.   : 5,509,421
DATED        : April 23, 1996
INVENTOR(S)  : Jeremy L. Muller, Gordon W. Neff, Joseph T. Pappalardo and G. Peter Pulsifer It is certified that error appears in the above-indentified patent and that said Letters Patent is hereby corrected as shown below:

Claim 3, column 8, line 41, delete "total" and substitute therefor -- fetal --.

Signed and Sealed this

Ninth Day of July, 1996

Attest:

BRUCE LEHMAN

*Attesting Officer*   *Commissioner of Patents and Trademarks*